United States Patent
He et al.

(10) Patent No.: US 8,415,406 B2
(45) Date of Patent: Apr. 9, 2013

(54) SETTING TIME INDICATOR FOR ACRYLIC BONE CEMENT

(75) Inventors: Shulin He, Montvale, NJ (US); Matthew P. Poggie, Upper Montclair, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1248 days.

(21) Appl. No.: 11/653,654

(22) Filed: Jan. 16, 2007

(65) Prior Publication Data

US 2007/0117878 A1    May 24, 2007

Related U.S. Application Data

(63) Continuation-in-part of application No. 11/187,724, filed on Jul. 22, 2005.

(51) Int. Cl.
  *A61K 6/083* (2006.01)
  *A61F 2/28* (2006.01)
  *C08F 2/50* (2006.01)

(52) U.S. Cl.
  USPC ........ 523/116; 424/423; 623/23.62; 525/298; 522/6

(58) Field of Classification Search .................. 523/113, 523/115, 116, 117; 522/75, 6; 424/423; 525/298
  See application file for complete search history.

(56) References Cited

U.S. PATENT DOCUMENTS

| | | | | |
|---|---|---|---|---|
| 4,261,879 | A * | 4/1981 | Kemper | 523/118 |
| 4,678,436 | A * | 7/1987 | Kondo et al. | 433/228.1 |
| 4,729,834 | A * | 3/1988 | Itoh et al. | 210/670 |
| 4,910,259 | A * | 3/1990 | Kindt-Larsen et al. | 525/259 |
| 5,302,627 | A | 4/1994 | Field et al. | |
| 6,017,983 | A | 1/2000 | Gilleo | |
| 6,291,547 | B1 | 9/2001 | Lyles et al. | |
| 6,444,725 | B1 | 9/2002 | Trom et al. | |
| 6,518,356 | B1 * | 2/2003 | Friese et al. | 524/580 |
| 6,689,826 | B2 | 2/2004 | Wojciak | |
| 6,756,421 | B1 * | 6/2004 | Todo et al. | 523/116 |
| 6,818,018 | B1 * | 11/2004 | Sawhney | 623/11.11 |
| 6,890,399 | B2 * | 5/2005 | Wojciak | 156/275.5 |
| 2002/0156483 | A1 * | 10/2002 | Voellmicke et al. | 606/93 |
| 2002/0164434 | A1 * | 11/2002 | Tarvin et al. | 427/500 |
| 2003/0139488 | A1 | 7/2003 | Wojciak | |
| 2005/0154081 | A1 * | 7/2005 | Yin et al. | 523/115 |
| 2005/0203217 | A1 * | 9/2005 | Pomrink | 523/451 |
| 2005/0256220 | A1 * | 11/2005 | Lavergne et al. | 523/115 |
| 2006/0293407 | A1 * | 12/2006 | Kuhn et al. | 523/116 |
| 2007/0021526 | A1 * | 1/2007 | He et al. | 523/116 |
| 2007/0031469 | A1 * | 2/2007 | Kuhn et al. | 424/423 |

FOREIGN PATENT DOCUMENTS

EP    1632211 A1 *    3/2006

* cited by examiner

*Primary Examiner* — Michael Pepitone
(74) *Attorney, Agent, or Firm* — Lerner, David, Littenberg, Krumholz & Mentlik, LLP

(57) ABSTRACT

A bone cement has a liquid acrylic monomer component, a powdered acrylic polymer component and yellowish beta-carotene (Pro-vitamin A) mixed into one of the liquid or powdered component and FDC blue No. 2 Lake powder mixed into the powdered component. The beta-carotene and FDC blue adds a greenish (yellow plus blue) color to the combined liquid and powdered component. The yellowish color disappears on setting of the bone cement leaving the cement blue.

24 Claims, 4 Drawing Sheets

Before  After

Before setting          Cured

Formula 1.                    Formula 2

SETTING TIME INDICATOR FOR ACRYLIC BONE CEMENT

CROSS-REFERENCE TO RELATED APPLICATIONS

This application is a continuation-in-part of U.S. application Ser. No. 11/187,724, filed on Jul. 22, 2005, the disclosure of which is incorporated herein by reference.

BACKGROUND OF THE INVENTION

This invention relates to a setting time indicator for acrylic bone cement. More particularly the acrylic bone cement of the invention indicates its setting point in situ by a change in its color, which change can be visually recognized.

Bone cements find wide usage in a variety of applications. For instance, they are used for cementing orthopedic implants in place, for the anchoring of endoprosthesis of the joints, for filling voids in bone, in the treatment of skull defects, and for the performance of spinal fusion. These cements are typically polymeric materials and more particularly acrylic polymers and the surgeon usually mixes the interactive components to make the cement at an appropriate stage during the surgical procedure.

Typically, the components of the bone cement comprise a powdered homopolymer or copolymer of methyl methacrylates, alkyl methacrylates and/or styrene and a suitable liquid monomer. The liquid monomer consists of esters of acrylic or methacrylic acid for example methyl methacrylate. The liquid monomer is typically provided in a glass ampoule. To accelerate the polymerization of the bone cement, a catalyst system may also be used. The catalyst, if present, is in the form of a redox catalyst system, usually containing an organic peroxy compound, such as dibenzoyl peroxide, plus a reducing component, such as p-toluidine. N, N-dimethylparatoluidine (DMPT) can also be used as a polymerization accelerator and hydroquinone (HQ) can be used as a stabilizer. The DMPT and HQ may be included with the liquid monomer. A radiopacifier such as barium sulphate may also be included.

After the bone is prepared the liquid and powdered components of the bone cement are mixed. The setting time is one of the most important characteristics of acrylic bone cement. The setting time is the point after mixing at which the cement is hardened. Although all bone cement manufacturers indicate the setting profile in their product inserts, the actual setting properties in an operating room (OR) may vary significantly due to different environmental conditions such as temperature, storage conditions and mixing methods. Therefore, it is sometimes difficult for cement users to predict when the cement sets in situ.

Surgeons or nurses have sometimes used excess cement to determine the setting point of the implanted cement by placing the cement on a surface in the OR or by holding it in their hands. The OR personnel use the time when the excess cement gets warm and hard to determine the setting point of the implanted cement. This assumes that the implanted cement behaves the same as the excess cement. Because of the different environmental factors, the setting time of the "bench" cement may be significantly different to that of the implanted cement. While it may be possible to determine the setting point in situ by monitoring the temperature rise of cemented implants during a cement setting process, such is difficult and inaccurate. It would be advantageous to have an acrylic bone cement available which indicates its setting point in situ.

One advantage for surgeons is that the recognition of the setting point of bone cement in situ prevents early loading of the joint, which may cause migration of implants. It may also eliminate unnecessary surgical site exposure time should the surgeon overestimate the setting time. Therefore, development of a cement that is able to indicate its setting point in situ would benefit both bone cement users and patients. In addition colored cements may help surgeons easily distinguish the bone cement from the surrounding tissues especially during revision surgery.

The setting process of acrylic bone cement is a free-radical polymerization reaction of methyl methacrylate (MMA) monomer. The bone cement sets when most of MMA monomer is converted to polymethyl methacrylate (PMMA) polymer through free-radical polymerization. By monitoring the free-radical polymerization of MMA monomer, one can determine the setting point of bone cement. Based on this rationale, the cement of the present invention uses color change to visually indicate the setting point in situ and also leaves a colored cement for visual identification.

Two color pigments, β-carotene (pro-vitamin A) and FDC blue No. 2 Lake, were used to formulate this colored cement. Carotene is a natural product that exist in plant and fruits and is a major source of Vitamin A. As an orange-red powder, it is soluble in organic solvents such as methyl methacrylate and gives a yellow-orange color. Carotene belongs to the category "exempt from certification" classified by FDA and is widely used in food industry as GRAS (Generally Regarded as Safe).

FDC blue No. 2 Aluminum Lake is a color additive that has been approved for use in acrylic bone cement in an amount of up to 0.1% (w/w). Methylene blue powder also may be used as we as chlorophyll which changes from light. It is insoluble in most solvents including water and methyl methacrylate. It has a good thermal stability and has been used in commercial bone cement products. It is supplied as a fine powder from Sensient Inc. of St. Louis.

As discussed above, acrylic bone cements are made from combining a powder polymeric component and a liquid monomer component and a polymerization initiator. One well known system is manufactured and sold by Howmedica Osteonics Corp. as Simplex® P bone cement. Heretofore, none of these types of systems have used color to indicate setting time.

U.S. Pat. No. 6,017,983 (Gilleo) relates to the use of a diazo dye that is believed to form a salt or complex with acid anhydrides, which acts as a color indicator for particular anhydride/epoxy resin thermoset adhesives. The resulting salt or complex is reported to produce a chromophoric shift in the dye which is indicative of the amount of acid anhydride present, and hence, the degree of cure. As the epoxy resin cures, the amount of acid anhydride diminishes, thus, producing a color change. This system appears to be limited to acid anhydride hardeners used to cure epoxy resins.

U.S. Publication No. 2003/0139488 (Wojciok) relates to a (meth) acrylate composition comprising a (meth) acrylate component; and a dye substantially dissolved in the (meth) acrylate component which imparts a first color to the (meth) acrylate component, wherein upon curing, a resultant cured composition has a second color. Preferably, upon curing, the resultant cured composition is substantially free of the first color.

SUMMARY OF THE INVENTION

It is one aspect of the present invention to provide a color indicator for setting time of an acrylic bone cement. In the preferred color indicator cement, a natural product called beta-carotene (Pro-vitamin A) is the compound which colors vegetables yellow or orange and is used as a pigment. This Pro-vitamin A is a well-known free radical scavenger and antioxidant. The Pro-vitamin A used herein is obtained from Aldrich Chemical Company. The basic structure of beta-carotene is made up of isoprene units. Its carbon-carbon conjugation system is eventually attacked by a free radical to lose its C—C conjugation during the bone cement setting process, resulting in its color change. Since only a small amount of Pro-vitamin A would be present in bone cement, the Pro-vitamin would participate in the free radical reaction only when most of MMA is consumed. Since the color change is caused by radical reactions of the isoprene units of the chemicals, the chemicals consisting of isoprene units that are susceptible to free radicals could be used in this application as a color indicator. For example, the compounds in a family of carotenoids such as lycopene and zeaxanthin could be candidates for color indicators for acrylic bone cements. These compounds have a lot of isoprene units and are well-known radical scavenges.

The invention relates to a bone cement which indicates its setting time via change in color and leaves a colored cement easily distinguishable from bone tissue. The bone cement comprises a liquid acrylic monomer component and a powdered acrylic polymer component, a polymerization accelerator and a first color additive, preferably yellowish beta-carotene, mixed into at least one of the liquid or powder components prior to or concurrently with its mixing. Between 5 and 500 ppm of the beta-carotene (0.0005% to 0.05% w/w) is preferably mixed into a liquid or powdered components. Of course, the beta-carotene could be mixed into both the liquid and powdered components. Preferably the liquid monomer comprises methylmethacrylate and the powdered component comprises a methylmethacrylate polymer. The liquid component comprises a monomer of an acrylic ester which when mixed with the beta-carotene and combined with FDC blue No. 2 Lake dye powder in the polymer powder forms a greenish color prior to setting and through free radical attack the beta-carotene loses its carbon-carbon bonds resulting in the color change from greenish to bluish.

A method for determining the setting time of an acrylic bone cement is also disclosed which includes mixing a liquid acrylic bone cement precursor and a powdered acrylic bone cement precursor having a blue dye therein with an additional yellow color additive, preferably beta-carotene. The color additives impart a first color to the bone cement (greenish). The beta-carotene color additive has carbon-carbon double bonds which break during polymerization causing a color change in the additive and consequently a bone cement having a different color than its initial color. Other carotenoids may also be used. In addition, other compounds that have carbon-carbon double bonds which are attacked by free radicals during polymerization causing the compound to lose or change color can be utilized. Since the blue dye does not undergo this change the final color of the cement is bluish.

DETAILED DESCRIPTION

Pro-vitamin A is a natural product that exists in plants and fruits, which are a major source of Vitamin A. It belongs to the category of "exempt from certification" classified by FDA and widely used in food industry as GRAS (Generally Regarded as Safe). Pro-vitamin is a yellow-orange fine powder that is soluble in many organic solvents such as methyl methacrylate. It can also be easily dispersed into bone cement powder.

Example 1

The color indicator cement (color cement) was prepared based on the formulation of Simplex® P bone cement. The color pigment can be either added in the Simplex® liquid monomer or dispersed in Simplex® cement powder. Alternatively, the color additive could be added by the surgeon on site as a separate component when he mixes either two components.

Pro-vitamin A is highly soluble in the Simplex® monomer (MMA) liquid component. Solid Pro-vitamin was directly added in Simplex® P liquid monomer, which turns the MMA monomer to yellow-orange. Pro-vitamin in an amount up to 50 ppm in Simplex P liquid component was examined in terms of color change and its effect on the setting properties of Simplex P bone cement. Formulations of the liquid component of color cements tested in this study are listed in Table 1. To get a 50 ppm mixture about 12 mg of beta-carotene was added to 200 ml of monomer, for a weight percent of 0.0062% w/w. The powder component of the color cement is the same as the standard Simplex® P powder described above.

TABLE 1 formulation of the liquid component

| | Ingredients | | | |
| --- | --- | --- | --- | --- |
| Cement | MMA (weight percent) | DMPT (weight percent) | HQ | Pro-vitamin |
| A | 97 | 2.6% | 75 ppm | 50 ppm |
| B | 97 | 2.6% | 75 ppm | 25 ppm |
| C | 97 | 2.6% | 75 ppm | 5 ppm |

The color indicator cement was examined at room temperature in terms of its color change. The cement was mixed in a mixing bowl following the Simplex® bone cement mixing instructions. The color of the cement before and after set was recorded and shown in FIG. 1.

Figure 1:
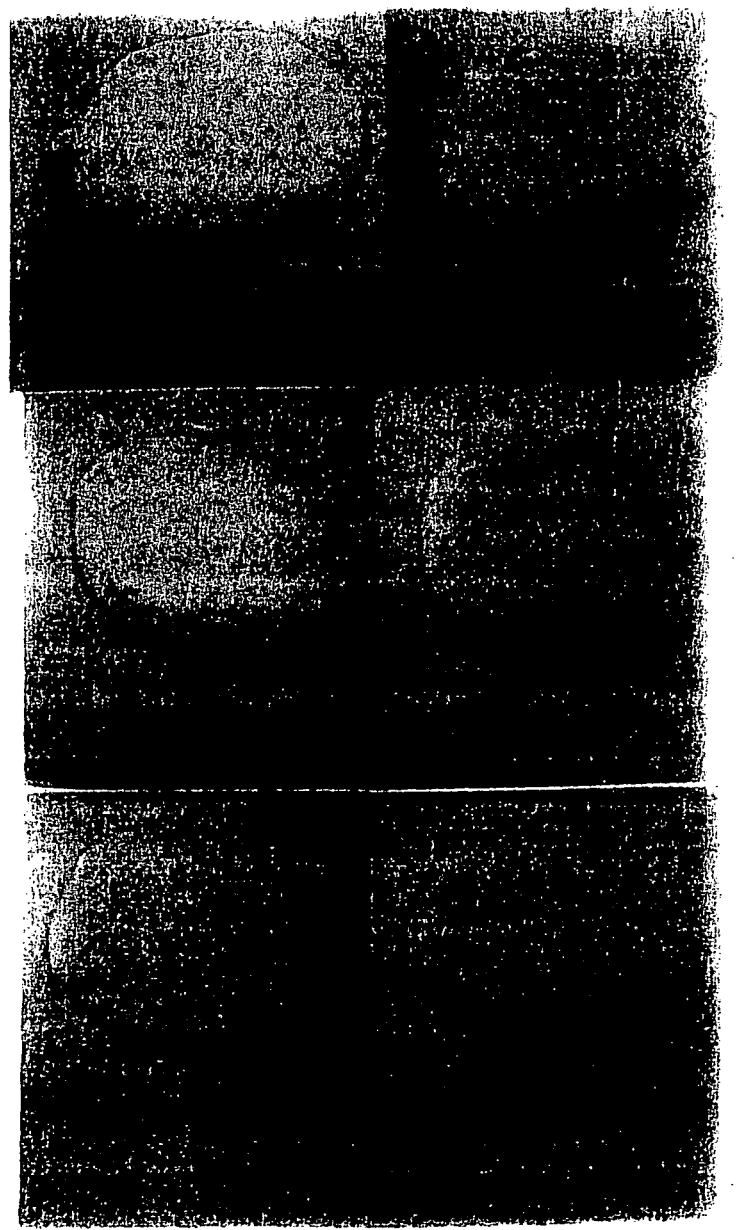
FIG. 1 shows a comparison of 50, 25 and 5 ppm mixtures of beta-carotene (Pro-vitamin A) in Simplex® P Mixed Bone Cement with the sample on the left hand side showing the bone cement prior to setting and the sample on the right hand side showing the sample after setting.

FIG. 1 shows the results of color profiling of the before and after setting. The images show clearly that the color cement turned to yellow at the onset of contact of the powder with the liquid component. When the bone cement set, the yellow color was gone. As the amount of Pro-vitamin A increases from 5 to about 50 ppm, the color of the cement paste got more intense and color change was more significant. It was also found that disappearance of color occurred in a short time period (less than 60 seconds). 100 ppm Pro-vitamin concentrations or even higher could be used as long as setting times are not unduly extended or physical cement properties are not greatly degraded. Mixing methods such as hand mixing and vacuum mixing did not affect the color change of the cement.

Figure 2:
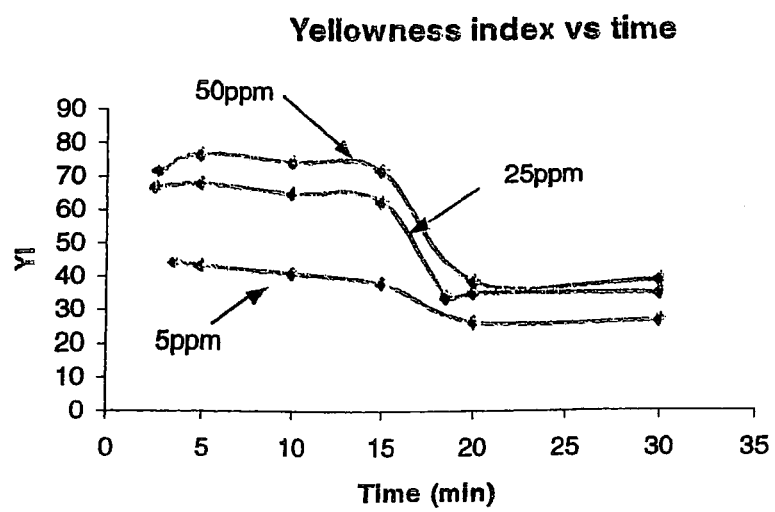
FIG. 2 shows the yellowness index versus time of the samples of FIG. 1.
Figure 3:
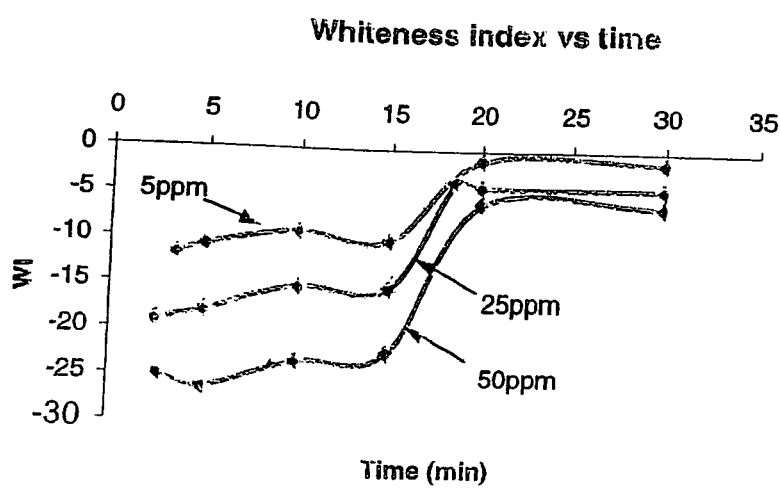
FIG. 3 shows the whiteness index verses time of the samples of FIG. 1.

Color change of the Pro-vitamin cement A was also measured by a spectrophotometer according to ASTM E313. Yellowness and whiteness index were recorded during the setting process, which are plotted versus time as shown in FIGS. 2 and 3. Both color indexes changed dramatically in a short time period that closely matched the clinical setting time test used by cement surgeons in the operating room. In this method a stopwatch was started at the onset of contact of the liquid monomer to the powder. The mixture is mixed at a clinical relevant temperature (usually 65° F. or 18.5° C.) and the resulting acrylic bone cement paste is held on a hand. The cement on a hand is occasionally kneaded until it gets hot. When it hardens enough to be knocked against a hard surface (wall or tables), it indicates that the cement reaches its setting point. The time at this point is the setting time of the cement. The results also show that the cement with 25 ppm and 50 ppm Pro-vitamin A changed its color more significantly than that with 5 ppm Pro-vitamin A.

FIGS. 2 and 3 show yellowness and whiteness index respectively versus the setting process of the Pro-vitamin cement. YI: Yellowness index—the degree of departure of an object color from colorless or from a preferred white toward yellow; WI: whiteness index:—the degree of departure of an object color from that of a preferred white.

Setting time, dough time and maximum temperature of the color cements were determined following the ASTM standard methods described in ASTM F451-95 and are shown in Table 2. The results demonstrated that Pro-vitamin A up to 50 ppm in Simplex® bone cement liquid component has no effect on the dough time, setting time and maximum temperature of Simplex® P bone cement.

TABLE 2

Setting properties of color indicator cement

| Color indicator cement | Setting Properties | | |
|---|---|---|---|
| | Dough (minutes) | Setting (minutes) | Tmax (° C.) |
| A | 3.00 | 11.86 | 80.3 |
| B | 3.00 | 11.21 | 73.3 |
| Control (No beta-carotene) | 3.00 | 11.84 | 79.4 |

Further examples were carried out to determine if the time at the disappearance of color matches the setting time of the bone cement. Both the standard ASTM method and clinical setting time method "knock" i.e. were examined. The results showed that the time when the yellow color disappeared closely matched the "knock" setting time, although it was approximately 30 seconds later than ASTM setting time.

Example 2

Pro-vitamin A in Simplex® powder component was also tested in terms of the color change and setting properties. 50 ppm (about 2 mg) Pro-vitamin A was added to 80 g and solid was directly blended with Simplex® P powder. The mixture was shaken for about 20 minutes in a shaker-mixture. The bone cement powder containing Pro-vitamin 50 ppm was evaluated. Since the amount of Pro-vitamin A was small, it did not change the appearance of the bone cement powder. The yellow color appeared during the mixing of liquid monomer with the powder component, and disappeared or faded when the cement set. The Pro-vitamin A in the powder component behaved similar as in the liquid monomer in terms of its color change and effect of on the setting properties of the bone cement. Setting time, dough time and maximum temperatures are shown in FIG. 3.

TABLE 3

Setting properties of color indicator cement

| Color indicator cement | Setting Properties | | |
|---|---|---|---|
| | Dough (minutes) | Setting (minutes) | Tmax (° C.) |
| A | 3.00 | 12.5 | 67.5 |

Example 3

Figure 4:
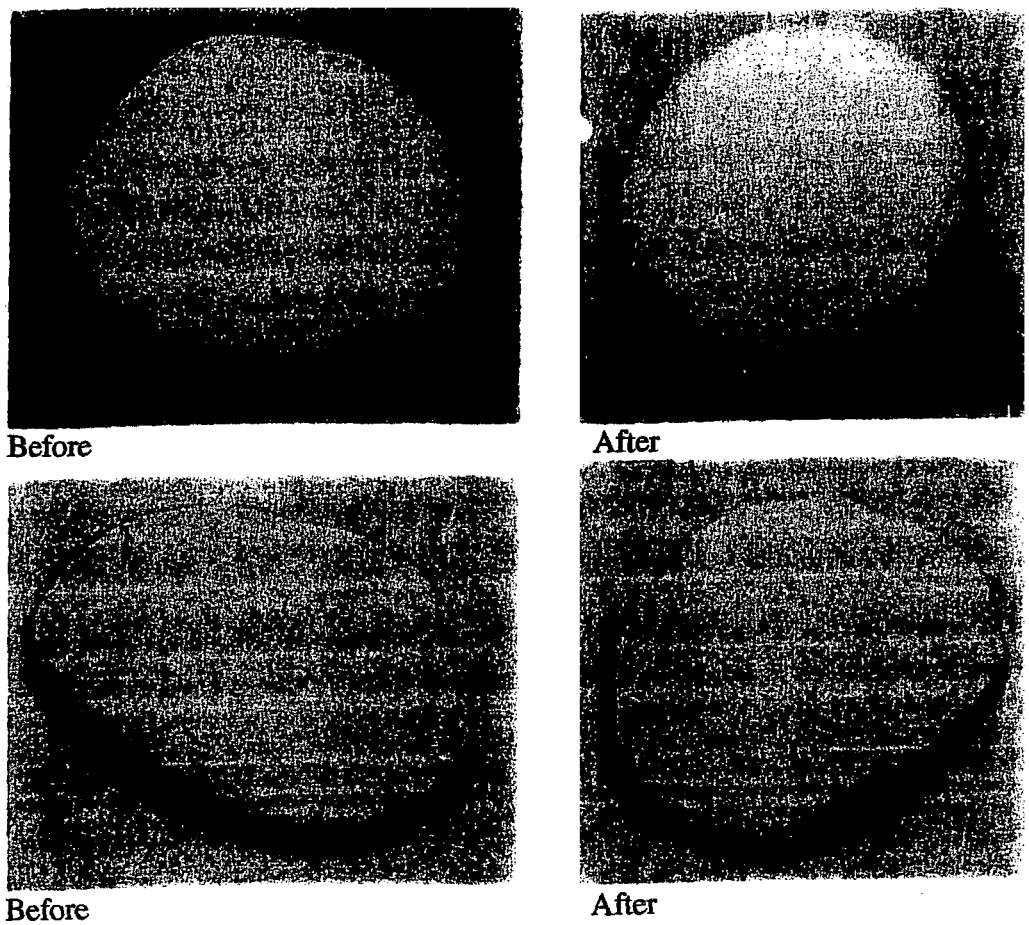
FIG. 4 shows the color change of two non-Simplex® P Bone Cements both before and after setting.

Pro-vitamin A was also tested for its color change in other bone cements including Biomet Palacos® R bone cement and DePuy® 1 bone cement. FIG. 4 shows the color change of Palacos® R and DePuy® 1 bone cements before and after cement set. Since Palacos® R is green, at least 50 ppm (preferably 100 ppm) Pro-vitamin A was required to demonstrate its color change. The colorant could be added to either liquid or blended in powder component. Pro-vitamin A up to 100 ppm did not show any effects on the setting properties of the cements.

Beta-carotene was added into a liquid monomer of both DePuy® 1 (25 ppm) and Palacos® R (100 ppm). The powdered components were then mixed with the monomer at room temperature. The cement pastes became yellow at mixing but changed to their original colors without the use of beta-carotene on setting.

FIG. 4. Color change of the cements before and after setting: up: DePuy 1 (approximately 25 ppm); low: Palacos R (approximately 100 ppm).

These examples demonstrated that Pro-vitamin (beta-carotene) can color acrylic bone cement by adding it either in the bone cement liquid component or dispersing it into the powder component. The formed color during mixing of the bone cement disappeared at the time when bone cement set, which visually indicated the setting point of the cement. This invention can be used in other powder-liquid acrylic bone cements such as Palacos® R, and DePuy® cements.

Example 4

Simplex P bone cement was used for preparation of the colored cement. The powder component of the colored cement was formulated by blending the blue color and powder with Simplex P powder. The formed powder became light blue. In this study, up to 0.05% (w/w) FDC blue No. 2 Lake was mixed in the powder and the powder was then sterilized via gamma irradiation at a production dose for commercial Simplex P bone cement.

The liquid component of the color cement was prepared by simply dissolving carotene powder in Simplex P monomer as discussed above. The liquid monomer solution became orange. In this study, up to 500 ppm carotene in the monomer was investigated. The powdered components were blended until the color was consistent.

Figure 5:
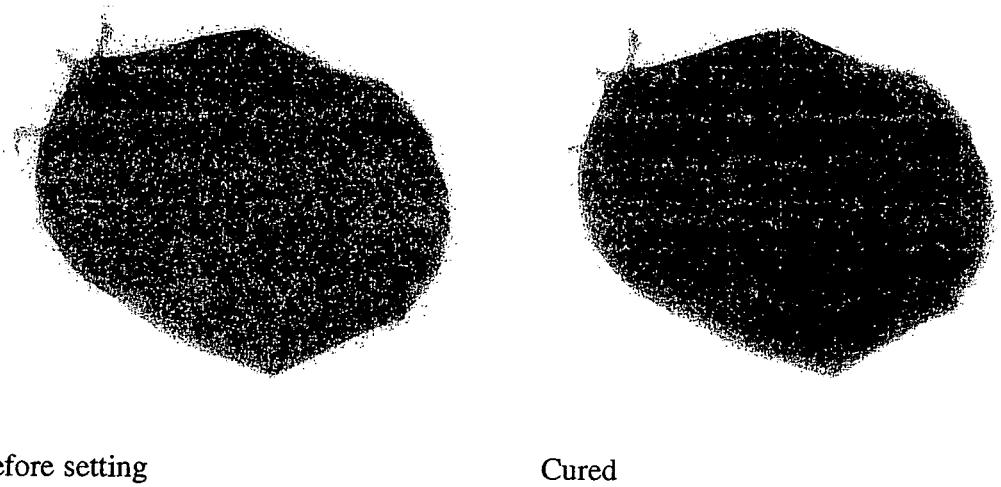
FIG. 5 shows images of before and after setting of colored cements having FDC blue No. 2 aluminum Lake 0.05% and 0.025% and beta-carotene 500 and 250 PPM.

Single dose of the powder component (40 grams) was mixed with 20 ml of the monomer containing carotene following the manufacturer's instruction for Simplex P bone cement. Mixing was conducted at room temperature (21° C.). In this example, the powder contained 0.05% FDC No. 2 Lake and 500 ppm carotene was present in the monomer. After mixing, the cement paste became green, a combination of blue color and orange color. The green color turned to blue at the time when the cement set. FIG. 5 shows the color of the cement before and after setting. Vacuum mixing was also tested and was found not to have an effect on the colored cement in terms of its color change.

Carotene pigment can also be blended in the Simplex P powder component. 10 mg carotene solid powder (equivalent to 500 ppm in liquid) was directly blended with 40 g Simplex P powder containing 0.05% FDC blue No. 2 Lake in a cement mixer (Mixevac III, Stryker Co). Since the amount of provitamin A was small, it did not change the appearance of the light blue bone cement powder. The green color appeared during the mixing of liquid monomer with the powder component, and it turned to blue when the cement set. Adding the Carotene to the powder or the monomer component had a similar effect on color change.

The setting process of acrylic bone cement is a free-radical polymerization reaction of MMA monomer. The bone cement sets when most of the MMA monomer is converted to PMMA polymer through free-radical polymerization.

The colored cement described in this invention, changes its color due to loss of the color from the carotene pigment during the setting process. Carotene molecules consist of a conjugated carbon-carbon double bond system as its chromophore. This conjugation system is susceptible to free radicals especially oxidation radicals. The chemistry of the color change in the color cement may be more complicated since there are probably carbon and peroxide radicals involved in the polymerization process. In general, the radicals generated during the bone cement setting process may react with the C=C conjugation system in carotene, resulting in breaking down of the conjugation system. Since a small amount of carotene is present in bone cement as compared to MMA monomore, it is anticipated that the carotene would participate in the reaction when most of the MMA is consumed. This explains that the color change occurs at the time when the cement gets hard i.e. when most of the MMA monomer is consumed.

Due to the loss of the color from carotene, the balance of the combined color shifts to the blue that is contributed by FDC No. 2 Lake. Either the initial color or the final color of the colored cement could be easily modified by altering the initial ratio of FDC blue No. 2 Lake and Carotene added to the cement.

Any colorants that undergo similar reaction may be considered as a candidate of a possible color indicator.

Color change of the colored cement was measured by a spectrophotometer according to ASTM E313. Two formulations were tested in this study. The whiteness and yellowness index were recorded during the setting process of the colored cement. These are plotted in FIG. 6.

Formula 1: 0.05% FDC blue No. 2 Lake in powder; 500 ppm carotene in the liquid monomer.

Formula 2: 0.025% FDC blue No. 2 Lake in powder; 250 ppm carotene in liquid monomer.

Figure 6:
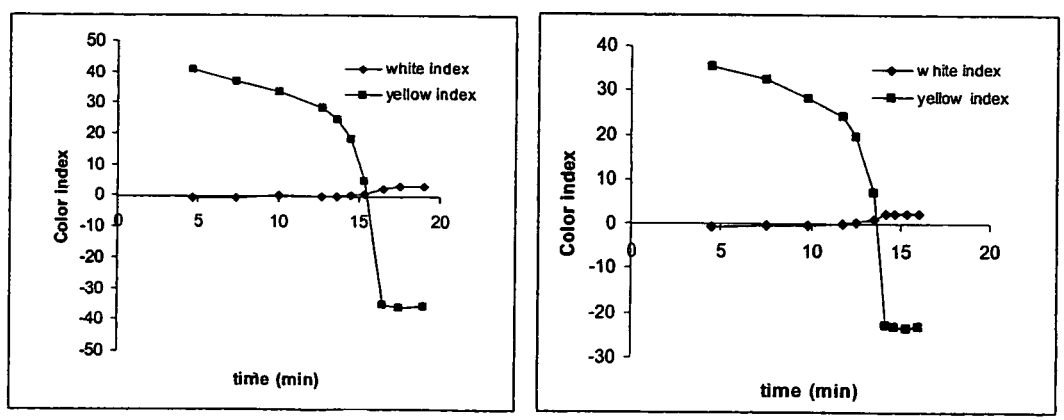
FIG. 6 shows two plots of the whiteness and yellowness index of two cement formulations during setting.

FIG. 6 shows the yellowness and whiteness index versus the setting process of the colored cement. YI: Yellowness Index—the degree of departure of an object color from colorless or from a preferred white toward yellow; WI: Whiteness Index—the degree of departure of an object color from that of a preferred white.

Yellowness index changed dramatically in a short time period that closely matched the setting time of the cement. Whiteness index was not sensitive to the change of color because the cement changed its color from green to blue.

A study was conducted to determine the effect of the color pigments on setting properties of the cement. The colored cement containing 0.05% (w/w) FDC blue No. 2 Lake in the powder component and 500 ppm carotene in the liquid component was tested in comparison with the same batch of Simplex P without color pigment. Setting time, dough time and maximum temperature of the colored cements were determined following the ASTM standard methods described in ASTM F451-95 and are shown in table 4. The experiment was conducted at environmental control room at 20° C., 50% RH. It was found that the colored cement containing up to 500 ppm carotene has no effect on the dough time and setting time It was also noted that change in color for the colored cement occurred just right at the time when the temperature of the color cement dramatically rose.

TABLE 4

Setting properties of color cement

| Cement | Carotene | Setting properties (n = 2) | | |
|---|---|---|---|---|
| | | Dough (min) | Setting (min) | Tmax (° C.) |
| Color cement 1 | 500 ppm | 4.3 | 15.7 | 67.7 |
| Color cement 2 | 250 ppm | 4.2 | 15.2 | 70.5 |
| Control cement | | 4.4 | 15.7 | 73.2 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone cement comprising:
   a liquid acrylic monomer component;
   a powdered acrylic polymer component;
   a polymerization accelerator;
   a beta-carotene (Pro=vitamin A) mixed into the liquid or powdered component in a concentration of 5 to 100 ppm;
   a blue color additive mixed into the powdered component.

2. The bone cement as set forth in claim 1 wherein the 5 and 100 ppm of beta-carotene is mixed into the liquid component.

3. The bone cement as set forth in claim 2 wherein the liquid monomer comprises an acrylic polymer.

4. The bone cement as set forth in claim 3 wherein the powdered component comprises a methylmethacrylate polymer.

5. The bone cement as set forth in claim 1 further comprising a stabilizer.

6. The bone cement as set forth in claim 5 wherein the stabilizer is hydroquinone.

7. The bone cement as set forth in claim 1 wherein the polymerization accelerator is N, N-dimethylparatoluidine.

8. The bone cement as set forth in claim 1 wherein the color additive is FDC Blue No. 2 Lake in an amount up to 0.1% (w/w) of the bone cement.

9. The bone cement as set forth in claim 8 wherein the beta-carotene comprises 0.0005% to 0.01% by weight of the liquid or powdered component.

10. A bone cement comprising:
   a liquid component including methyl methacrylate monomer;
   a powdered methacrylate polymer component;
   beta-carotene mixed in one of the liquid or powdered components in a concentration of between 0.5 to 100 ppm; and
   FDC blue No. 2 Lake mixed in one of the liquid or powder components.

11. The bone cement as set forth in claim 10 wherein the beta-carotene comprises 5 to 100 ppm of the liquid of powdered component.

12. The bone cement as set forth in claim 10 wherein the FDC blue No. 2 Lake is in the powdered component and makes up to 0.1% (w/w) thereof.

13. A bone cement comprising:
   a liquid component comprising a monomer of an acrylic ester;
   a powdered component comprises a methyl methacrylate polymer which when mixed with said liquid component polymerizes and sets to form a hardened bone cement and
   a first and second color additives which impart a first color upon mixing with said liquid and powdered component and a second color upon setting of said bone cement.

14. The bone cement as set forth in claim 12 wherein the first color is a combination of the first and second color additives and the second color is only the color of the second color additive.

15. The bone cement as set forth in claim 14 wherein the first color additive is beta-carotene (Pro-vitamin A) and the second color additive is FDC blue No. 2 Lake.

16. The bone cement as set forth in claim 15 wherein the beta-carotene comprises 0.0005% to 0.05% by weight of the liquid or powdered component.

17. The bone cement as set forth in claim 15 wherein the first color is green and the second color is blue.

18. The bone cement as set forth in claim 13 wherein the first color additive has carbon-carbon double bonds which are attacked by free radicals during polymerization causing it to lose its color.

19. The bone cement as set forth in claim 18 wherein the first color additive is a carotenoid and the second color additive is FDC blue No. 2 Lake.

20. The bone cement as set forth in claim 14 wherein the first color additive is beta-carotene (Pro-vitamin A).

21. A method for determining the setting time of an acrylic bone cement comprising:
   mixing a liquid acrylic bone cement precursor and a powdered acrylic bone cement precursor and first and second color additives imparting a first color, a first of the color additives having carbon-carbon double bonds which break during polymerization causing a color change in the first color additive; and
   allowing the mixture to set to form a bone cement having the color of the second additive.

22. The method as set forth in claim 21 wherein the first color additive is added to the liquid precursor and the second color additive is added to the powdered precursors prior to said mixing step.

23. The bone cement as set forth in claim 22 wherein the first color additive is a carotenoid and the second is FDC blue No. 2 Lake.

24. The bone cement as set forth in claim 23 wherein the compound is beta-carotene (Pro-vitamin A).

* * * * *